United States Patent [19]

Zupancic et al.

[11] Patent Number: 4,855,375

[45] Date of Patent: Aug. 8, 1989

[54] STYRENE TERMINATED MULTIFUNCTIONAL OLIGOMERIC PHENOLS AS NEW THERMOSETTING RESINS FOR COMPOSITES

[75] Inventors: Joseph J. Zupancic, Bensenville; Andrew M. Zweig, Schaumburg; James A. Wrezel, Buffalo Grove, all of Ill.

[73] Assignee: Allied-Signal Inc., Morris Township, Morris County, N.J.

[21] Appl. No.: 276,598

[22] Filed: Nov. 28, 1988

Related U.S. Application Data

[63] Continuation-in-part of Ser. No. 87,921, Aug. 21, 1987, abandoned.

[51] Int. Cl.$^4$ ............................................. C08F 16/32
[52] U.S. Cl. .................................. 526/247; 526/286; 526/313
[58] Field of Search ..................... 526/247, 286, 313

[56] References Cited

U.S. PATENT DOCUMENTS 4,116,936  9/1978  Steiner .............................. 526/286

*Primary Examiner*—Christopher Henderson
*Attorney, Agent, or Firm*—Eugene I. Snyder; Harold N. Wells; Jay P. Friedenson

[57] ABSTRACT

Thermosetting resins which are essentially vinylbenzyl end-capped ethers of the oligomeric condensation products of certain dihydric phenols and formaldehyde are readily polymerized to give an extensively cross-linked polymer particularly useful in printed circuit boards and similar laminates. Effective cost reduction may be enjoyed by replacing up to 50% of the vinylbenzyl moieties by other groups, such as alkyl and benzyl groups, without destroying the usefulness of the resulting thermosetting resins. The vinylbenzyl ether product from bisphenol-A is especially recommended.

13 Claims, No Drawings

STYRENE TERMINATED MULTIFUNCTIONAL OLIGOMERIC PHENOLS AS NEW THERMOSETTING RESINS FOR COMPOSITES

CROSS REFERENCE TO RELATED APPLICATION

This application is a continuation-in-part of our co-pending application, Ser. No. 087,921, filed Aug. 21, 1987, all of which is incorporated by reference, now abandoned.

BACKGROUND OF THE INVENTION

The subject matter of this application is directed toward resins used in the manufacture of reinforced plastics. More particularly, the resins (binders) are used in the preparation of composites formed from fibers embedded in a polymer resin matrix. Even more specifically this application is directed toward the use of such resins in the preparation of circuit board laminates where the reinforcing material is glass or quartz fiber.

To overcome some mechanical and structural limitations of plastics it has become relatively commonplace to reinforce them with other components. Composites formed of various fibers embedded idn a polymer resin matrix are especially useful and susceptible to enormous variation depending upon the nature of the fiber used, how the fiber is utilized, and the matrix or binder for the fibers. Materials which have been used as fibers include glass, quartz, oriented polymers such as the aramids (Kevlar[198]), graphite and boron. Whatever their composition such fibers can be used as chopped or continuous filaments, and when used as continuous filaments they can all be unidirectional or woven into a fabric. The matrix can be, for example, a polyester, epoxy, polyimide, polyetherketone or polyetherimide resin as either a thermoset or thermoplastic material. The uses for such composites range from airframes to tennis rackets and from boat hulls to rocket motor casings.

A particular area of composite application is that of printed circuit boards, especially multilayer circuit boards, for mounting electronic components. The use of glass fabric as the reinforcing material has become more-or-less standard and epoxy resins are most often used as the matrix. For the fiber to exert a reinforcing action it is necessary that the fibers be completely coated with resin, and to achieve this the glass fiber often is surface treated to provide sites for chemical bonding to the resin or to its precursor or for otherwise improved adhesion to the matrix material.

Multilayer circuit boards are laminates with alternating layers of composite and etched copper sheet. A brief discussion of their manufacture will aid in apprciating the propeties requisite for such boards. A woven glass fabric is first impregnated with resin by dipping the cloth in a resin solution, often referred to as the varnish soslution, in what is called the A-stage. Solvent is thenr emoved to afford a glass cloth reinforced resin, or pre-preg, in which is called the B-stage. In some cases the resin int he ppreg may be partially cured, in other cases uncured, but in all cases the prpreg is a non-tacky, readily handled rigid sheet of glass cloth embedded in and coated with a resin. The finished circuit board is prepard by laminating alternating layers of prepreg and eched copper foil under conditions of temperature and pressure where resin is cured, i.e., further polymerized and crosslinked to a final unfusible, insoluble stage (C-stage).

From the above brief description some necessary and desirable characteristics of the resin may be readily discerned. The circuit board will be subjected to soldering temperatures and may be operated at an elevated temperature, or experience cyclic locally elevated temperatures because of local power generation, and thus the thermal coefficient of expansion of the reisn should approximate that of glass to ensure continued dimensional stability and resistance to heat distortion. The resin should have a high solubility in the varnish solution to ensure high resin loading. The varnish soslution should have a sufficiently low viscosity for even coating but not too low a viscosity as to run off the fibers. It is necessary that the prepreg not be tacky so that it can be readily handled and stored. The resin is desirably non-crystalline for enhanced solubility in the varnish solution and for good film forming properties in the pre-preg. The resin should have adequate flow at the C-stage so as to make void-free laminated bonds, with the curing temperature somewhat higher than the glass transition temperature ($T_g$) of the resin to afford a wider processing "window". The resin also should be chemically resistant to a corrosive environment and to water vapor. To ensure that the discrete electrical componenots on a circuit board interact only via the etched path on the copper foil, it is desirable that the matrix have a low dielectric constant and high resistance.

The invention to be described is an amorphous, thermosetting resin which affords a varnish solution of high solids content with a viscosity leading to even coating without runoff, which affords a non-tacky prepreg, has a glass transition temperature sufficiently below the curing temperature to afford an adequate window of processing, and which shows excellent flow properties at the C-stage. The final lcured resin nexhibits a low dielectric constant and dissipation factor, a low coefficient of thermal expansion, and a high glass transition temperature. In short, we believe our cured resin has propeties superior to hose currently recognized as industry standards in the lamination of circuit boards, and thus presents outstanding benefits.

U.S. Pat. No. 4,116,936 describes thermosetting resins which are vinylbenzyl ethers of monomeric phenols, of simple phenol-formaldehyde condensation products commonly known as novolac resins, and of oligomers resulting from tthe reaction of adihydric phenol, such as bisphenol A, and a glycidyl ether. However much these resins may represent an advance over prior art resins, presumably because the fully cured product shows, among other desirable properties, greater hydrolytic stability and corrosion resistatnce, we have discovered resins whose properties are decidedly superior in several operational aspects. In particular, whereas the resins of our invention show desirable flow at prepreg temperatures, they exhibit higher flow viscosity in solution at ambient temperature, thereby minimizing runoff and leading to improved coating uniformity. Additionally, the fully cured products of our resins show an improved coefficient of thermal expansion, a particularly important propety in laminate production. Thermal expansion is a poorly understood function of the nature of the polymer backbone as well as the nature of the end capping group. The coefficient of thermal expansion can not be predicted, and obtaining thermosetting resins whose theroset product has a coefficient of thermale xpansion similar to that of, e.g., woven glass fabric remains a hit-or-miss affair. For our purposes an ideal fully cured product will have a coefficient of thermal expansion of about 30 ppm. The materials of our invention approach the goal closely.

The thermosetting resins of this invention do not appear to have a close analogue in the prior art, with the most relevant art of Wang et al., US. Pat. No. 4,707,558, only distantly related. The formulae of the patentees encompass a very large niverse of permutations, and in the case where in their formula II m'=0 and m=1 one has a structure which is arguably, and only weakly arguably, pertinent to the materials of this invention. But even within such restrictions one requires a judicious choice of other of the patentees' variables, especially A and X, to arrive at materials even then ony remotely related to our invention.

It needs to be emphasized that although this application will stress the utilization of the resins of our invention in the production of multilayer circuit boards, the resins may be useful in fabricating composites generally. Consequently, it needs to be explicitly recognized that the resins of our invention are intended for composite manufacture without any limitations other than those imposed by the product specifications themselves.

SUMMARY OF THE INVENTION

The purpose of our invention is to provide thermosetting resins whose properties make them desirable in the preparation of composites, especially in laminated multilayer boards of a glass fiber in a polymer matrix. An embodiment comprises the vinylbenzyl ethers ofo the oligomeric condensation product of certain dihydric phenols and nformaldehyde. In a ore specific embodiment the dihydric phenol is what is commonly known as bisphenol-A. In a more specific embodiment the vinylbenzyl ether is a mixture of meta- and para-substituted with amethyl group. In still another embodiment from about 50 to 100% of the ether moieties are vinylbenzyl ether moieties, with the remainder being primary alkyl moieties containing from 1 to about 4 carbon atoms. Other embodiments will become apparent from the following description.

DESCRIPTION OF THE INVENTION

Our invention is a class of thermosetting resins of vinylbenzyl ethers of the oligomeric condensation products of a dihydric phenol and formaldehyde where from 50 to 100% of the ether groups are vinylbenzyl moieties and the remainder, if any, are alkyl moieties containing 1 to 10 carbon atoms or the benzyl moiety. Especially where all the ether moieties are the vinylbenzyl group, the extensively cross-linked polymers resulting from curing the thermosetting resins of this invention have improved properties with regard to their use in printed circuit boards. In particular, they have a dielectric constant which is better than conventional materials, a coeffcient of thermal expansion which is better than conventional materials, show excellent solvent resistance (low water pickup), exhibit an improved glass transition temperature, and have a higher flow viscosity in solution at room temperature relative to conventional materials. Our thermosetting resins may be depicted by the formula,

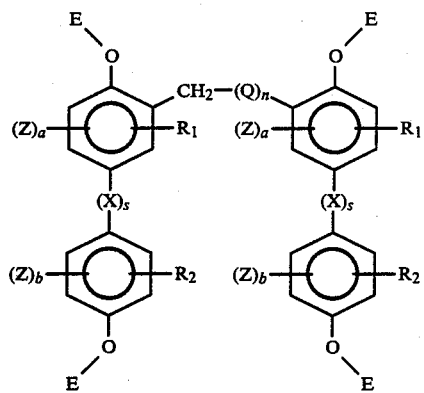

The resins of this invention result from the etherification of oligomers which are the condensation product ofa dihydric phenol and formaldehyde. Therefore the product will be a mixture of materials with varying molecular weight, that is, the resulting resins are mixtures having discrete components of differing degrees of oligomerization. What needs to be emphasized is that the reins are a mixture of oligomers, and the number, n, of recurring units Q generally will vary from 0 to 10. That is, n is 0 or an integer from 1 to 10, where in the prferred practice of our invention it is 0 or an integer from 1 to 6. As previously mentioned, a spectrum of oligomers typically result from the condensation reaction, and in a desirable branch of our invention the number average of n is about 3, i.e., from 0 to about 5.

The recurring unit Q itself has the structure,

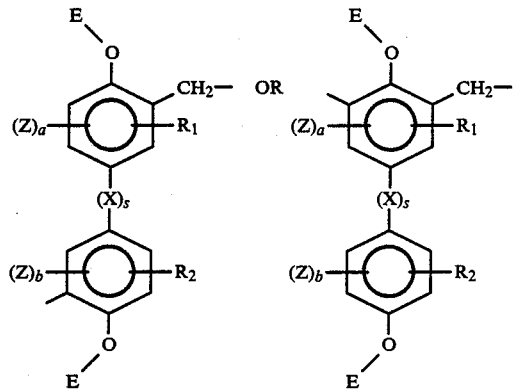

Note that the condensation may occur either on the same ring, as in the right hand structure, or in different rings, as in the left hand structure. The aromatic rings in the recurring unit Q are either joined directly or are separated by an intervening atom furnished by the moiety X. Therefore, s is 0 or 1.

Each of the moieties X may be either a methylene [$CH_2$], isopropylidene [$C(CH_3)_2$], hexafluoroisopropylidene [$C(CF_3)_2$], an oxygen, sulfur, sulfonyl [$S(O)_2$], carbonyl [$C(0)$], or a dioxyphenylene group [$OC_6H_4O$], where the oxygens of the latter generally are para or meta to each other. In a favored embodiment is isopropylidene.

Each of the aromatic rings may bear substituents or may be completely unsubstituted. Thus, $R_1$ and $R_2$ are independently selected from moieties such as hydrogen, alkyl moieties containing from 1 to 10 carbon atoms, the phenyl moiety alkoxy moieties containing from 1 to 10 carbon atoms, and phenoxy, $C_6H_5O$. Examples of suitable alkyl moieties include methyl, ethyl, propyl, butyl, pentyl, hexyl, heptyl, octyl, nonyl, and decyl moieties. The methyl and tert-butyl groups are preferred alkyl moieties in the practice of our invention, although hte variant where $R_1=R_2=H$ is quite desirable.

The basic resins also can be readily modified to be flame retardant by incorporating halogen atoms into the aromatic rings. Thus, Z may be a halogen atom, especially bromine, and where the aromatic ring is halogenated a and b is an integer from 1 to 4. Polyhalogenated materials are desired as flame retardants, which means that a and b are recommended to be 2, 3, or 4. Where the aromatic rings are not halogen substituted then both a and b are 0.

The oligomeric condensation products have a multiplicity of phenolic hydroxyl groups substantially all of which are end-capped as either groups in our thermosetting resins. The best case results where the ether portion, E, is a vinylbenzyl moiety, that is, of the structure.

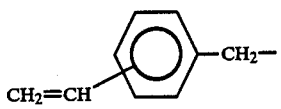

which may be either the meta- or para-isomer, and which usually is a mixture of othe meta- and para-isomers. However desirable it may be to have all the phenolic hydroxyls end-capped with vinylbenzyl moieties, there is a decided cost advantage when fewer than all of the ether groups are vinylbenzyl, usually at the expense of a somewhat lower dielectric constant. In our invention it is required that at least 50% of the E moieties be a vinylbenzyl moiety, but a product with better performance characteristics results when from 70 to 100% of the ether groups are vinylbenzyl, and the best product results when 95 to 100% of such groups are vinylbenzyl.

In those cases where less than all of the ether groups are vinylbenzyl, then we are partial to resins where E is an alkyl group containing from 1 to 10 carbons or oa benzyl group. Where E is an alkyl group, the primary alkyl groups are given priority, especially the primary lower alkyl groups containing from 1 to 4 carbon atoms. Thus, the most desirable alkyl groups consist of methyl, ethyl, 1-propyl, 1-butyl, and 1-methyl-1-propyl. Other alkyl groups are represented by 1-pentyl, 1-hexyl, 1-heptyl, 1-octyl, 1-nonyl, 1-decyl, 2-methyl-1-butyl, 3-methyl-1-butyl, 2,3-dimethyl-1-butyl, 3,3-dimethyl-1-butyl, 2-methyl-1-pentyl, and so forth. However, it is to be emphasized that a benzyl group also operates quite satisfactorily in the practice of our invention.

The resins of our invention may be prepared by acid catalyzed condensation of dihydric phenols with formaldlehyde followed by end-capping substantially all the pneolic hydroxyls by converting them to ethers. Acid catalyzed condensation is preferred to avoid the formation of terminal hydroxy methylene groups, —$CH_2OH$. End-capping by ether formation can be effected by any suitable means, such as by reating the phenolic condensation product with an alkyl or benzyl halide in a basic medium. The resulting thermosetting resins are readily polymerized with attendant crosslinking by a variety of curing means. In a preferred mode, curing is effected by thermal means, generally autoinitiated by heating the resin in air at a temperature between abou 100 and 250°C., and more particularly between about 120 and 200°C. In practice multilayer boards may be laminated at a temperature between abou 150 and 200°C. for 0.5-5 hours with postcuring ata bout 180-250°C. for about 0.5-24 hours. Curing also may be brought about by chemical means using a free radical initiator such as azo-bis-isobutyronitrile, benzoyl peroxide, di-t-butyl peroxide, etc. Curing may be effected as well by irradiation, especially by visible and ultraviolet light in the presence of a suitable photoinitiator. Whether thermal, chemical, or photochemical curing is performed, the resin becomes extensively cross-linked and sets to an infusible, insoluble glassy solid.

The materials of our invention also can be blended with other types of vinylbenzyl ethers of functionality greater than or equal to 2 to provide A-stage varnish solutions with tailorable viscosity and variable properties in the cured product such as glass transition temperature, heat distortion temperature, fracture toughness, etc. For example, our resins could be blended with various styrenated bisphenols to raise cross-link density and improve processability of the bis-styryl compound. The materials of our invention are polymers of moderate functionality (i.e., number of vinylbenzyl groups per molecule) and viscosity and they can be incorporated to reduce crystallinity of various styrenated bisphenols where the bisphenols are exemplified by the formula

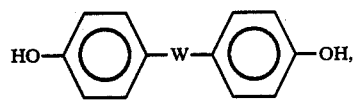

with W being —O—, —$C(CH_3)_2$—, $SO_2$—, —CO—, and so forth to raise the resin solids content in the A-stage varnish solution, to raise the resin content in the B-stage, and to reduce the amount of resin flow in the C-stage. High-to-moderate molecular weight poly(vinylbenzyl ethers) also may be useful for improving the shelf life of other styrenated oligomers, and may raise the ductility of the otherwise brittle laminate, such as in the case of styrenated bisphenol A.

The following examples are merely illustrative of our invention and are not limiting in any way.

EXAMPLE 1

Preparation of Styrene Terminated Bisphenol-A Formaldehyde (STBPA-F). Bisphenol-A formaldehyde resin was prepared as follows. 150.0 g (0.658 moles) of bisphenol-A was dissolved in 500 ml of ethanol in a 1 liter round bottom flask equipped with condenser and magnetic stirrer. To his reaction mixture was added 0.5 ml of concentrated sulfuric acid. The solution was heated to reflux and then 14.5 g (0.151 moles) of paraformaldehyde was added gradually to the reaction. The reaction was heated at reflux with stirring for 48 hours and then allowed to cool to room temperature. The reaction was neutralized with aqueous sodium hydroxide solution and then concentrated under vacuum, yielding 130.3 g of viscous syrup, with a $M_w=362$.

50.0 g (0.1062 moles) of bisphenol-A formaldehyde resin and 71.35 g (0.4675 moles) vinylbenzyl chloride (60/40 meta/para isomer ratio) were dissolved in 110 ml of acetone in a three neck-round bottom flask equipped with condenser, addition funnel, thermometer, mechanical stirrer and nitrogen purge. The reaction mixture was heated at reflux (65-70°C. temperature) for a period of one hour, following which a solution of 41.83 g (0.746 moles) of potassium hydroxide in 93 ml of methanol was added to the warm reaction mixture over an internal of one hour. The reaction was stirred thereafter at ambient temperature for a period of 24 hours. The reaction mixture was recovered, dried over magnesium sulfate, filtered, and concentrated under vacuum. The resulting oil was dried in a vacuum oven at ambient temperature overnight and yielded 24.5 g of resin.

EXAMPLE 2

Preparation of Cured STBPA-F. 3.3 g of STBPA-F of Example 1 was placed in a flat casting dish and cured by heating in an oven at a temperature of 120°C. for a period of 2 hours, followed by a 16 hour cure at 160°C. and a 2 hour cure at 200°C. Following this, the sample was then post-cured for a period of 2 hours at 225°C. and recovered. The cured polymer was found to have a glass transition temperature (Tg) of greater than 300°C., a minor softtening point (Tsp) (measured via Thermal Mechanical Analysis (TMA)) at 165 ±5°C., a coefficient of thermal expansion from 25° to 165°C. of 40±2 ppm/°C and from 25° to 260°C. of 65±3 ppm/°C. The dielectric constant at 1 MHz and dissipation factor at 0% and 50% relative humidity are summarized in the following table.

TABLE 1

| Relative Humidity | Dielectric Constant | Dissipation Factor |
|---|---|---|
| 0% | 2.94 ± 0.27 | 0.004 ± 0.001 |
| 50% | 3.25 ± 0.17 | 0.013 ± 0.001 |

EXAMPLE 3

Preparation of Cured STBPA-F from chloroform Solution. 2.0 g of STBPA-F resin of Example 1 was dissolved in about 10 milliliters of ochloroform. The resulting solution was transferred to a flat castingn dish and heated on a hot plate to remove a major portion of the chloroform solvent. The sample was then cured in an oven at 120°C. for 2 hours, followed by 16 hours at 160°C. and 2 hours at 200°C.. The sample was post cured at 225°C. for 1 hour. The cured polymer was found to have the following properties: glass transition temperature (Tg) >300°C., coefficient of thermal expansion from 25 to 260°C. ($a_{260}$) of 59±4 ppm/°C. and a dielectric constant and dissipation factor (1 MHz) at 0% relative humidity of 2.63 ±0.17 and 0.007±0.001, respectively.

EXAMPLE 4

Preparation of Styrene Terminated Polybrominated Bisphenol-A Formaldehyde (STBBPA-F). 40.57 (0.086 moles) of bisphenol-A formaldlehyde resin, 40 milliliters of carbon tetrachloride, 84 milliliters of methanol and 1.99 g of potassium bromide were charged into 500 ml three neck-round bottom flask equipped with condenser, addition funnel, nitrogen purge and magnetic stirring bar. The reaction vessel was placed in a water bath and heated to a temperature of about 50°C. To this 2-phase reaction mixture was added 41.25 milliliters (0.800 moles) of bromine dropwise over a 4 hour period. At the end of this time 80 milliliters of water was added to the reaction mixture and a distillation head attached to the reaction vessel, and the volatile products were distilled off at atmospheric pressure. The remaining residue was taken up in 160 milliliteres of dichloromethane and the organic phase was washed three times with 80 milliliters of water and then twice with 80 milliliteres of 10% aqueous sodium bisulfite to remove any residual bromine which may be present. The organic phase was washed with 80 milliliters of water and dried over sodium sulfate. The methylene chloride was removed under vacuum and then azeotropic drying with ethanol gave 80.70 grams of product.

40.0 g (0.425 moles) of the above polybrominated bisphenol-A formaldehyde resin and 28.54 g (0.187 moles) of vinylbenzyl chloride (60/40 meta/para isomer ratio) were dissolved in 90 ml of acetone in a three neck-round bottom flask equipped with condenser, addition funnel, thermometer, mechanical stirrer and nitrogen purge. The reaction mixture was heated to reflux (65-70°C. temperature) for a period of one hour, following which a solution of 12.54 g (0.224 moles) of pottassium hydroxide in 28 milliliteres of methanol was added to the warm reaction mixture over a period of one hour. Thereafter the reaction was stirred at ambient temperature for a period of 24 hours. The reaction mixture was recovered, dried over magnesium sulfate, filtered and concentrated under vacuum. The resulting oil was dried in a vacuum oven at ambient temperature overnight and yielded 30.8 g of resin.

EXAMPLE 5

Preparation of Cured STBBPA-F. 5.0 gof STBBPA-F resin of Example 4 wazs placed in a flat casting dish and cured by heating in an oven at a temperature of 120°C. for 2 hours, followed by a 16 hour cure at 160° C. and a 2 hour cure at 200°C. The sample was post-cured for a period of 2 hours at 225°C. and recovered. The cured polymer was found to have the following properties: glass transition temperature (Tg)>250°C., and dielectric constant (1 MHz) and dissipation factor at 0 to 50% relative humidity as tabulated in Table 2.

TABLE 2

| Relative Humidity | Dielectric Constant | Dissipation Factor |
|---|---|---|
| 0% | 3.01 ± 0.16 | 0.002 ± 0.001 |
| 50% | 2.98 ± 0.02 | 0.009 ± 0.001 |

EXAMPLE 6

Preparation of Cured STBBPA-F from chloroform Solution. 2.0 g of STBBPA-F resin of Example 4 was dissolved in 10 milliliters of chloroform. The resulting solution was transferred to a flat casting dish and heated on a hott plate to remove the majority of the solventt, the sample was then cured in an oven at 120°C. for 2 hours, followed by 16 hours at 160°C. and 2 hours at 200°C. The sample was post-cured at 225°C. for 1 hour. The cured polymer was found to have the following properties: glass transition temperature (Tg)>250°C., and dielectric constant and dissipation factor at 0% and 50% relative humidity as tabulated in table 3.

TABLE 3

| Relative Humidity | Dielectric Constant | Dissipation Factor |
|---|---|---|
| 0 | 2.82 ± 0.16 | 0.004 ± 0.002 |
| 50 | 2.77 ± 0.008 | 0.012 ± 0.001 |

EXAMPLE 7

Preparation of Cured STBPA; Comparison of Selected Propeties. Styrene terminated bisphenol-A was prepared according to the method of Steiner (U.S. Pat. No. 4,116,936) by reacting vinylbenzyl chloride with bisphenol-A. This resin was cured by taking 2.0 g of STBPA and was dissolved in about 10 milliliters of chloroform in a flat casting dish and heated on a hot plate to remove the majority of the solvent. The sample was then cured in an oven at 120°C. for 2 hours, followed by 16 hours at 160°C. and 2 hours at 200°C.. The sample was postcured for 1.5 hours at 225°C.. The cured polymer had the following properties: glass transition tempeature (Tg)>250° C, minor softening point (Tsp) (measured via TMA) at 168 ±11° C., a coefficient of thermal expansion from 25°to 168° C. of 57 ±8 ppm/°C. and from 25°to 260° C. of 71 ±23 ppm/°C.. The dielectric constant at 1 MHz and dissipation factor at 0% and 50% relative humidity are summarized in the following table.

TABLE 4

| Relative Humidity | Dielectric Constant | Dissipation Factor |
|---|---|---|
| 0 | 2.93 ± 0.11 | 0.003 ± 0.002 |
| 50 | 3.15 ± 0.14 | 0.013 ± 0.001 |

What is claimed is:

1. A thermosetting resin which is a vinylbenzyl ether of the oligomeric condensation product of a dihydric phenoland formaldlehyde and with the formula:

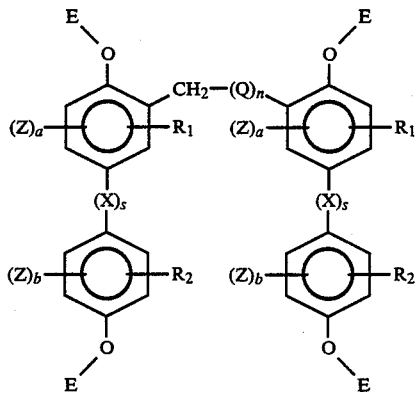

where the recurring unit Q has the structure,

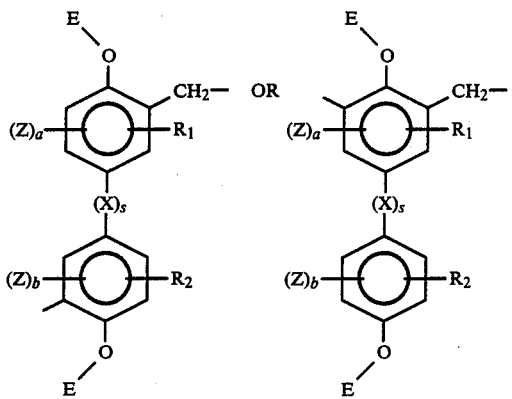

and n is an integer from 1 to 10;

s is 0 or 1;

each X is independently selected from the group consisting of $CH_2$, $C(CH_3)_2$, $C(CF_3)_2$, $S(O)_2$, and $OC_6H_4O$;

each $R_1$ and $nR_2$ is independently selected from the group consisting of hydrogen, alkyl and alkoxy moieties containing 1 to 10 carbon atoms, phenyl and phenoxy;

a and b are independently 0 or integers from 1 to 4;

Z is Cl or Br;

E is selected from the group consisting of the vinylbenzyl moiety, alkyl moieties containing 1 to 10 carbona toms, or benzyl, subject to the constraint that at least 50% of all E's are the vinylbenzyl moiety.

2. The resin of claim 1 where each $R_1$ and $R_2$ is selected from the group consisting of hydrogen, methyl, and tert-butyl moieties.

3. The resin of claim 2 where all $R_1$ and $R_2$ are hydrogen.

4. The resin of claim 2 where all $R_1$ and $R_2$ are methyl.

5. The resin of claim 1 where s is 1 and X is $C(CH_3)_2$.

6. The resin of claim 1 where Z is Br and each of a and b is an integer from 1 to 4.

7. The resin of claim 1 where E is primary alkyl moiety containing from 1 to 10 carbon atoms.

8. The resin of claim 7 where the alkyl moietty containsn 1 to 4 carbon atoms.

9. The resin of claim 1 where E is benzyl.

10. The resin of claim 1 where from 70 to 100% of the E mooieties are the vinylbenzyl moiety.

11. The resin of claim 10 where from 95 to 100% of the E moieties are vinylbenzyl moieties.

12. The resin of claim 1 where n is an integer from 1 to 6.

13. The resin of claim 1 where the number average of n is about 3.

* * * * *

UNITED STATES PATENT AND TRADEMARK OFFICE
CERTIFICATE OF CORRECTION

Page 1 of 4

PATENT NO. : 4,855,375
DATED : Aug. 8, 1989
INVENTOR(S) : Zupancic et al.

It is certified that error appears in the above-identified patent and that said Letters Patent is hereby corrected as shown below:

Column 1, line 26: "idn" should read --in--
line 32: "Kevlar198" should read --Kevlar$^{TM}$--
line 55: "apprciating" should read --appreciating--
line 56: "propeties" should read --properties--
line 59: "solustion" should read --solution--
line 59: "thenr" should read --then--
line 60: "emoved" should read --removed--
line 61: "which" should read --what--
line 62: "int he ppreg" should read --in the prepreg--
line 63: "prpreg" should read --prepreg--
line 66: "prepard" should read --prepared--
Column 2, line 1: "unfusible" should read --infusible--
line 9: "reisn" should read --resin--
line 13: "soslution" should read --solution--
line 26,27 "compone-nots" should read --components--
line 37: "lcured" should read --cured--
line 37: "nexhibits" should read --exhibits--
line 41: "propeties" should read --properties--
line 41: "hose" should read --those--
line 48: "tthe" should read --the--
line 48: "adihydric" should read --a dihydric--

UNITED STATES PATENT AND TRADEMARK OFFICE
CERTIFICATE OF CORRECTION

PATENT NO. : 4,855,375

DATED : Aug. 8, 1989

INVENTOR(S) : Zupancic et al.

It is certified that error appears in the above-identified patent and that said Letters Patent is hereby corrected as shown below:

| | | |
|---|---|---|
| Column 2, | line 53: | "resistatnce" should read --resistance-- |
| | line 62: | "propety" should read --property-- |
| | line 67: | "theroset" should read --thermoset-- |
| | line 68: | "thermale xpansion" should read --thermal expansion-- |
| Column 3, | line 10: | "niverse" should read --universe-- |
| | line 16: | "ony" should read --only-- |
| | line 33: | "ofo" should read --of-- |
| | line 34: | "nformaldehyde" should read --formaldehyde-- |
| | line 34: | "ore" should read --more-- |
| | line 39: | "amethyl" should read --a methyl-- |
| | line 61: | "coeffcient" should read --coefficient-- |
| Column 4, | line 20: | "ofa" should read --of a-- |
| | line 26: | "reins" should read --resins-- |
| | line 29: | "prferred" should read --preferred-- |
| | line 63: | after "embodiment" insert --X-- |
| Column 5, | line 6: | "hte" should read --the-- |
| | line 30: | "othe" should read --the-- |
| | line 44: | "oa" should read --a-- |
| | line 50: | "1-methyl-1-propyl" should read --2-methyl-1-propyl-- |
| | line 57,58: | "formaldlehyde" should read --formaldehyde-- |

UNITED STATES PATENT AND TRADEMARK OFFICE
CERTIFICATE OF CORRECTION

PATENT NO. : 4,855,375

DATED : Aug. 8, 1989

INVENTOR(S) : Zupancic et al.

It is certified that error appears in the above-identified patent and that said Letters Patent is hereby corrected as shown below:

| | | |
|---|---|---|
| Column 5, | line 59: | "pneolic" should read --phenolic-- |
| | line 63: | "reating" should read --reacting-- |
| Column 6, | line 2: | "abou" should read --about-- |
| | line 4: | "abou" should read --about-- |
| | line 5: | after "and" insert --about-- |
| | line 5: | "ata bout" should read --at about-- |
| Column 7, | line 5: | "internal" should read --interval-- |
| | line 5: | after "thereafter" insert --at-- |
| | line 36: | "chloroform" should read --Chloroform-- |
| | line 38: | "ochloroform" should read --chloroform-- |
| | line 39: | "castingn" should read --casting-- |
| | line 55: | "formaldlehyde" should read --formaldehyde-- |
| | line 68: | "milliliteres" should read --milliliters-- |
| Column 8, | line 2: | "milliliteres" should read --milliliters-- |
| | line 19: | "pottassium" should read --potassium-- |
| | line 19: | "milliliteres" should read --milliliters-- |
| | line 30: | "gof" should read --of-- |
| | line 31: | "wazs" should read --was-- |
| | line 49: | "chloroform" should read --Chloroform-- |
| | line 53: | "hott" should read --hot-- |
| | line 53: | "solventt" should read --solvent-- |
| | line 61: | "table" should read "Table" |

UNITED STATES PATENT AND TRADEMARK OFFICE
CERTIFICATE OF CORRECTION

Page 4 of 4

PATENT NO. : 4,855,375
DATED : Aug. 8, 1989
INVENTOR(S) : Zupancic et al.

It is certified that error appears in the above-identified patent and that said Letters Patent is hereby corrected as shown below:

Column 9, line 5: "Propeties" should read --Properties--
line 17: "tempeature" should read --temperature--
line 38: "phenoland" should read --phenol and--
line 38: "formaldlehyde" should read --formaldehyde--
Column 10, line 23: "$nR_2$" should read --$R_2$--
line 31: "carbona toms" should read --carbon atoms--
line 46,47: "moietty containsn" should read --moiety contains--
line 50: "mooieties" should read --moieties--

Signed and Sealed this

Nineteenth Day of November, 1991

Attest:

HARRY F. MANBECK, JR.

Attesting Officer   Commissioner of Patents and Trademarks